United States Patent [19]
Huebner

[11] Patent Number: 5,624,440
[45] Date of Patent: Apr. 29, 1997

[54] COMPACT SMALL BONE FIXATOR

[76] Inventor: Randall J. Huebner, 18560 SW. Hart Rd., Aloha, Oreg. 97005

[21] Appl. No.: 587,210

[22] Filed: Jan. 11, 1996

[51] Int. Cl.$^6$ .................................................. A61B 17/60
[52] U.S. Cl. .................................................. 606/59; 606/54
[58] Field of Search .................................. 606/54, 55, 56, 606/57, 58, 59, 60, 61, 72, 73

[56] References Cited

U.S. PATENT DOCUMENTS

| | | |
|---|---|---|
| 583,455 | 6/1897 | Bush . |
| 1,201,864 | 10/1916 | Overmeyer . |
| 1,789,060 | 1/1931 | Weisenbach . |
| 2,214,490 | 9/1940 | Thomas . |
| 2,250,417 | 7/1941 | Ettinger . |
| 2,251,209 | 7/1941 | Stader . |
| 2,333,033 | 10/1943 | Mraz . |
| 2,371,519 | 3/1945 | Haynes . |
| 2,391,537 | 12/1945 | Anderson . |
| 2,391,693 | 12/1945 | Ettinger . |
| 2,393,694 | 1/1946 | Kirschner . |
| 2,393,831 | 1/1946 | Stader . |
| 2,393,982 | 2/1946 | Giesen . |
| 2,406,987 | 9/1946 | Anderson . |
| 2,434,431 | 1/1948 | Pincock . |
| 2,435,850 | 2/1948 | Siebrandt . |
| 2,443,106 | 6/1948 | Grosso . |
| 2,697,433 | 12/1954 | Zehnder . |
| 3,128,768 | 4/1964 | Geistauts . |
| 3,244,170 | 4/1966 | McElvenny . |
| 3,835,849 | 9/1974 | McGuire . |
| 3,862,631 | 1/1975 | Austin . |
| 3,961,854 | 6/1976 | Jaquet . |
| 3,975,032 | 8/1976 | Bent et al. . |
| 4,003,096 | 1/1977 | Frey . |

(List continued on next page.)

FOREIGN PATENT DOCUMENTS 2086231  5/1982  United Kingdom .

OTHER PUBLICATIONS

"TMJ Implants: Lessons for All of Us," Stan Mendenhall, *Orthopedic Network News*, vol. 6, No. 2, Apr. 1995.
"The Use of Mini Fixation in the Hand," G. Asche, *Clinical Techniques in Upper Extremity*, pp. 505–520 date unknown.
"A Simple External Fixator for Use in Metacarpal and Phalangeal Fractures: A Technique Paper," D. H. Sochart and A. S. Paul, *Journal of Orthopaedic Trauma*, vol. 9, No. 4, pp. 333–335.
"Distal Radius Fractures," by John M. Agee, MD, *External Fixation*, vol. 9, No. 4, Nov. 1993, pp. 577–585.

(List continued on next page.)

*Primary Examiner*—Guy V. Tucker
*Attorney, Agent, or Firm*—Kolisch, Hartwell, Dickinson, McCormack & Heuser

[57] ABSTRACT

A compact external fixator used to repair small bone fractures which includes an elongate cylindrical support rod to which are mounted a pair of articulation assemblies. Each assembly is held to the support rod by a rod clamp which, in a loosened condition, can rotate about and translate along the support rod. When tightened, the clamps fix the positions of the articulation assemblies relative to the rod. A pin carrier block is pivotally attached to each rod clamp to pivot about a first pivot axis that is perpendicular to and offset from the rod. As with the clamp, the pivotal motion of the block can be selectively fixed or loosened. Each block further includes a generally planar circular pin mounting shelf with a central axis normal to the plane of the shelf. The plane of the shelf is substantially parallel to and offset from the first pivot axis. A generally planar and disk-like pin clamp ring is disposed centered coaxially over the central axis of each pin shelf. Each ring includes a first face in which are formed a pair of spaced apart, parallel pin guide tracks, with the first face being disposed toward and spaced apart from the pin shelf. A pair of pins is captured between the first face and the pin shelf, with the pins located in the pin guide tracks. The pins and pin clamp rings are rotatable about the central axis of the pin shelf until the ring is tightened.

15 Claims, 3 Drawing Sheets

U.S. PATENT DOCUMENTS

| | | |
|---|---|---|
| 4,040,130 | 8/1977 | Laure . |
| 4,127,119 | 11/1978 | Kronner . |
| 4,135,505 | 1/1979 | Day . |
| 4,220,146 | 9/1980 | Cloutier . |
| 4,244,360 | 1/1981 | Dohogne . |
| 4,271,832 | 6/1981 | Evans et al. . |
| 4,299,212 | 11/1981 | Goudfrooy . |
| 4,308,863 | 1/1982 | Fischer . |
| 4,338,927 | 7/1982 | Vokov et al. . |
| 4,349,017 | 9/1982 | Sayegh . |
| 4,393,868 | 7/1983 | Teague . |
| 4,409,970 | 10/1983 | Carrel . |
| 4,475,546 | 10/1984 | Patton . |
| 4,483,334 | 11/1984 | Murray . |
| 4,488,542 | 12/1984 | Helland . |
| 4,548,199 | 10/1985 | Agee . |
| 4,611,586 | 9/1986 | Agee et al. . |
| 4,628,919 | 12/1986 | Clyburn . |
| 4,662,365 | 5/1987 | Gotzen et al. .................. 606/59 |
| 4,922,896 | 5/1990 | Agee et al. . |
| 4,978,348 | 12/1990 | Ilizarov .................. 606/57 |
| 4,988,349 | 1/1991 | Pennig . |
| 5,254,078 | 10/1993 | Carter et al. . |
| 5,304,177 | 4/1994 | Pennig . |
| 5,320,622 | 6/1994 | Faccioli et al. . |
| 5,320,623 | 6/1994 | Pennig . |
| 5,454,810 | 10/1995 | Pohl et al. .................. 606/59 |

OTHER PUBLICATIONS

"History of External Fixation," *Complications of External Skeletal Fixation*, pp. 3–11 Author and date unknown.

"Limb Lengthening Surgical Technique Using the Hoffmann™ External Fixation Device," Harold M. Dick, MD, brochure. Howmedica, Date unknown.

"Current Concepts of External Fixation of Fractures," Hans K. Uhthoff, pp. 96 and 143. 1982.

Fractures in the Pectoral Limb, p. 143. Author and date unknown.

General Principles of Fracture Treatment, p. 171. Author and date unknown.

"The Closed Treatment of Common Fractures," John Charnley, pp. 227–229. 1957, Second Ed.

5,624,440

COMPACT SMALL BONE FIXATOR

FIELD OF THE INVENTION

This invention relates generally to a bone fixator for reducing and stabilizing fractures and other traumas in small bones. More particularly, the invention is directed to a compact small bone fixator adapted for use in external fixation of fractures of small bones, such as those in the hand.

BACKGROUND OF THE INVENTION

It has become commonplace to use external fixators to repair various injuries and defects in bones. Such fixators are typically mounted on two or more transcutaneous pins embedded into the bone on opposite sides of the fracture or defect. An external frame is used to control the position and orientation of the pins relative to one another. The external frame typically will allow the positions of the pins to be adjusted in any of several degrees of freedom. By proper manipulation of the pins, it is possible to accurately and securely reduce the severed ends of the bone so that healing may be effected.

A major drawback with known fixators is the lack of freedom for placement of the pins. In particular, known fixators generally require the surgeon to choose the pin placement to accommodate the fixator being used. For many common types of fractures, this is not a problem because of the predictable presentations. For avulsion or other severe injuries to the hand and fingers, however, the ideal pin placement does not fit any predefined pattern. In addition, the pins should be installed through uninjured skin, further limiting acceptable pin placements. Thus, when treating such injuries, it is desirable to have a fixator that can accommodate a wide range of pin placement combinations as dictated by the nature of the injury rather than the mechanics of the fixator.

Because fixators remain in place on the patient's hand for considerable periods of time, it is important that the fixator be as compact and unobtrusive as possible. Moreover, the small size of the bones in the hand dictates that the fixator should allow the pairs of pins to be placed very close to one another. A fixator for use in the hand should also permit pins of various sizes to be used. Thus, small pins should be accommodated where there are small bones or bone fragments. Larger bones, on the other hand, may require larger pins to achieve adequate stability. One additional desirable property of a fixator for use on the hand is the ability to expand the fixator to hold additional pins at more than two locations. Lastly, a small bone fixator should work with either threaded pins or Kirshner wires, the latter being a standard inventory item in a variety of sizes at most hospitals.

SUMMARY OF THE INVENTION

The present invention is a compact external fixator used to repair small bone fractures and includes an elongate cylindrical support rod to which a pair of articulation assemblies are mounted. Each assembly is held to the support rod by a rod clamp which, in a loosened condition, can rotate about and translate along the support rod. When tightened, the clamps fix the positions of the articulation assemblies relative to the rod. A pin carrier block is pivotally attached to each rod clamp to pivot about a first pivot axis that is perpendicular to and offset from the rod. As with the clamp, the pivotal motion of the block can be selectively fixed or loosened. Each block further includes a generally planar circular pin mounting shelf with a central axis normal to the plane of the shelf. The plane of the shelf is substantially parallel to and offset from the first pivot axis. A generally planar and disk-like pin clamp ring is disposed centered coaxially over the central axis of each pin shelf. Each ring includes a first face with a pair of spaced apart, parallel pin guide tracks formed therein, with the first face being disposed toward and spaced apart from the pin shelf. A pair of pins is captured between the first face and the pin shelf, with the pins being located in the pin guide tracks. The pins and pin clamp rings are rotatable about the central axis of the pin shelf until the ring is tightened.

Many other features, advantages and additional objects of the present invention will become manifest to those versed in the art upon making reference to the detailed description which follows and the accompanying sheets of drawings in which preferred embodiments incorporating the principles of this invention are disclosed as illustrative examples only.

DETAILED DESCRIPTION OF THE PREFERRED EMBODIMENTS

Figure 1:
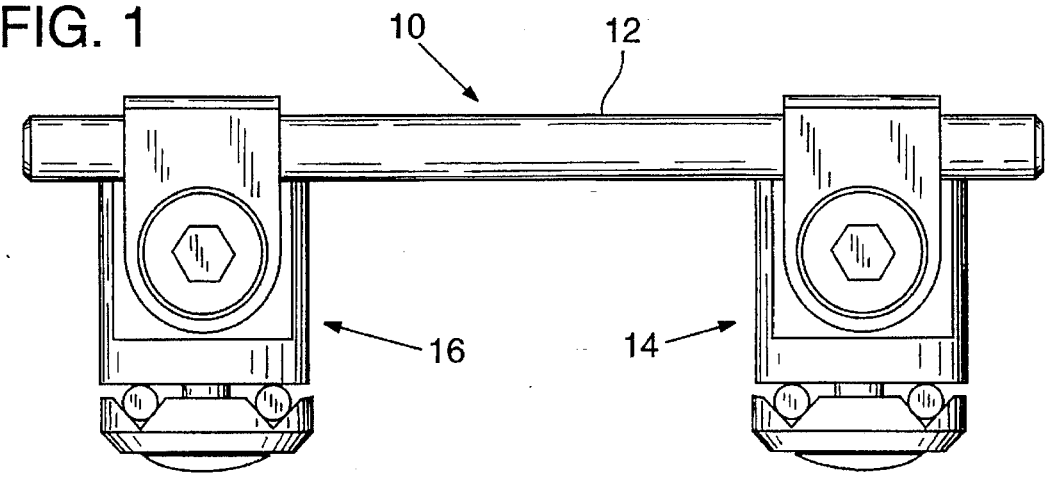
FIG. 1 is a top view of a fixator constructed according to the present invention.
Figure 2:
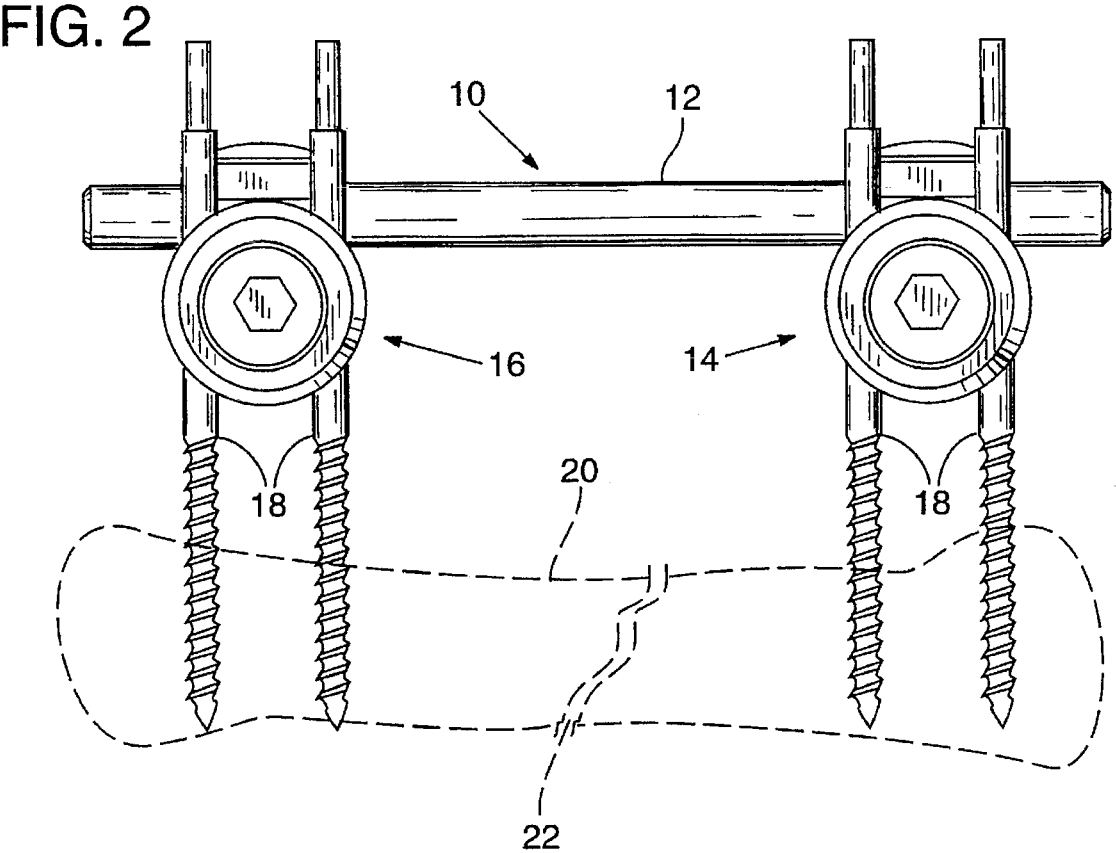
FIG. 2 is a front view of the fixator of FIG. 1 further showing the fixator mounted to a bone.

A compact external bone fixator according to the present invention is shown generally at 10 in FIGS. 1 and 2. Fixator 10 includes a support rod 12 coupling two pin articulation assemblies 14, 16. Each assembly carries two pins 18 with the pins from assembly 14 being engaged in a bone 20 on the opposite side of a fracture 22 from the pins of assembly 16. Note that the pins are shown with threads in FIG. 2, but fixator 10 may be used with either smooth or threaded pins. Because the assemblies are articulated, as will be described below, the relative positions of the pins can be adjusted to achieve the desired pin placement and thereafter reduce the fracture. Once the fracture is properly reduced, the assemblies are secured in a fixed configuration to stabilize the fracture during healing.

Figure 3:
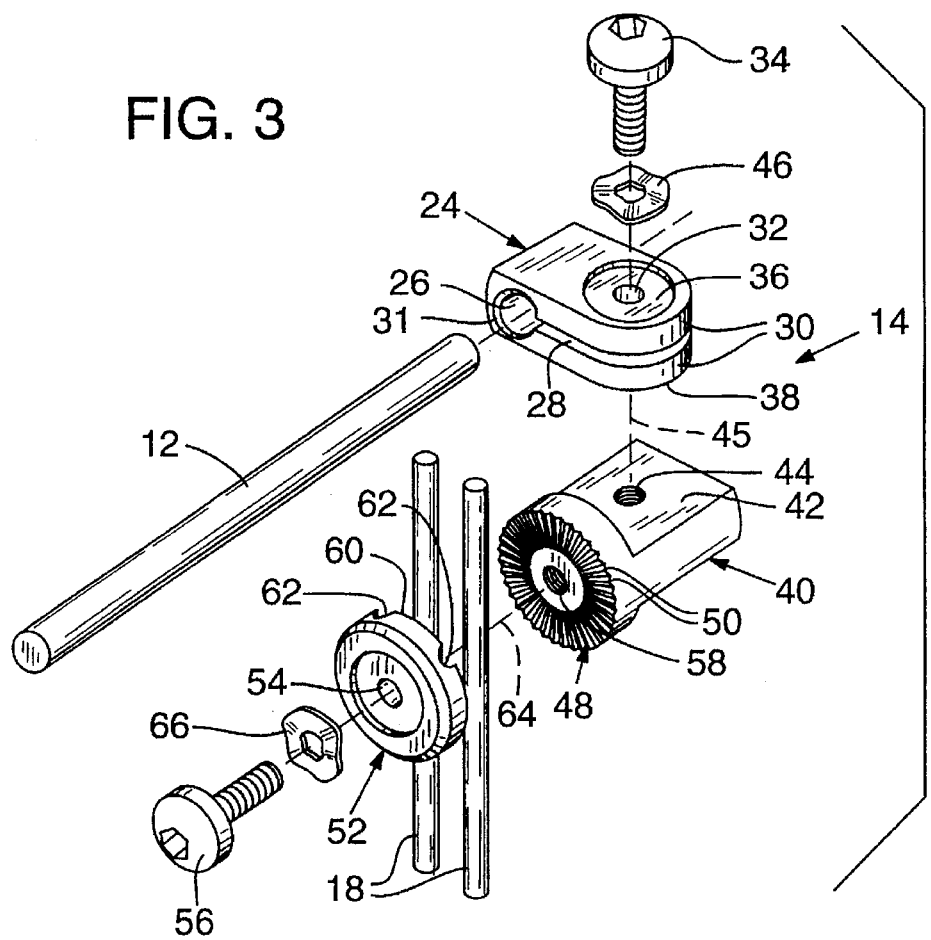
FIG. 3 is an exploded view of an articulation assembly according to the present invention.
Figure 4:
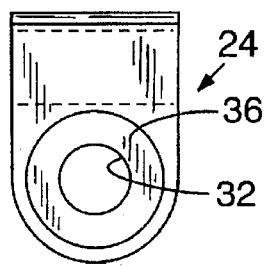
FIG. 4 is a top view of a rod clamp according to the present invention.
Figure 5:
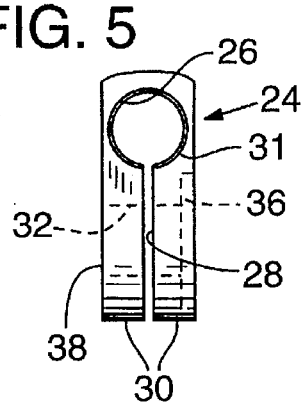
FIG. 5 is a side view of the rod clamp of FIG. 4.

The two assemblies are of substantially identical construction and, therefore, the following discussion will be made with reference to assembly 14 as shown in FIG. 3. A U-shaped rod clamp 24, illustrated in FIGS. 4–5, couples assembly 14 to rod 12. Clamp 24 includes a cylindrical passage 26 formed near the closed end of the U. A slot 28 extends from passage 26 to the opposite end of the clamp thereby separating a pair of legs 30. Passage 26 fits over rod 12 to allow assembly 14 to slide along and rotate about the rod. The ends of passage 26 include a chamfer 31 to ease insertion of the rod into the passage. When the legs are urged toward one another, the diameter of the passage is reduced slightly so that clamp 24 grips the rod, preventing further movement.

A bore 32 extends through both legs and the slot in a direction perpendicular to the slot and the axis of passage 26. Bore 32 is adapted to receive a screw 34 which extends therethrough, one face of the clamp forming a support surface 36 for the head of the screw and the other face forming a bearing surface 38. See FIG. 5. In the preferred embodiment, the axis of the screw is offset from the axis of passage 26 by approximately 0.2 inches.

Figure 6:
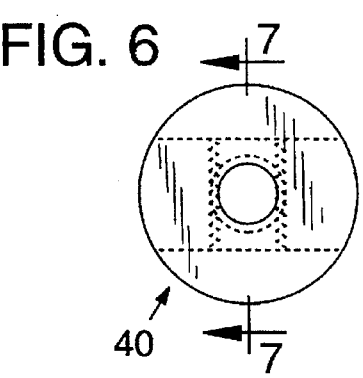
FIG. 6 is a front view of a pin carrier block according to the present invention.
Figure 7:
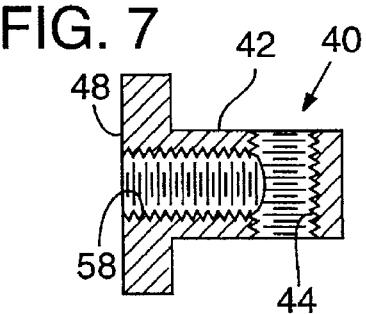
FIG. 7 is a section view of the pin carrier block of FIG. 6 along line 7—7.

Screw 34 pivotally couples clamp 24 to a pin carrier block 40. Block 40, shown in FIGS. 6–7, includes a bearing surface 42 which is held against bearing surface 38 of clamp 24 by the screw. A threaded bore 44 extends into block 40 to receive the screw. Until the screw is tightened, the bearing surfaces ride against each other and block 40 can be pivoted about a first pivot axis 45, which is coaxial with the axis of the screw. When the screw is tightened, however, the friction between the bearing surfaces is increased, locking the orientation between the block and the clamp. Moreover, because the screw simultaneously urges the legs of the clamp together, the clamp is also locked in place on the rod as the screw is tightened.

It should be noted that a resilient washer in the form of a wave washer 46 is provided in the preferred embodiment between the head of screw 34 and support surface 36. This arrangement causes some tension to be maintained when the screw is loosened slightly which allows the block and the clamp to be moved with application of slight force, but prevents "flopping" of the pieces. This feature is important because it makes adjustment and positioning of the fixator much easier.

Block 40 includes a pin shelf 48 against which pins 18 are disposed. Shelf 48 is generally flat and circular and is parallel to and offset from the first pivot axis. In the preferred embodiment, the offset is about 0.3 inches. A number of serrations 50 are formed in the surface to the shelf to help maintain a secure grip on the pins. Pins are held against the pin shelf by a pin clamp ring 52. Ring 52, which is generally disk-like, includes a central aperture 54 through which a screw 56 extends and engages a threaded bore 58 formed in the center of shelf 48.

An inner face 60 of ring 52 is disposed toward the pins and includes a pair of parallel V-shaped pin guide tracks 62, one on each side of aperture 54. Tracks 62 fit partway over the pins to stabilize their position under the ring. (In the preferred embodiment, the angle of the V of the tracks is 110-degrees and the depth is 33 thousandths of an inch.) Such tracks allow the pin carrier block to accommodate a wide range of pin sizes: from 0.034 to 0.078 inches.

Because ring 52 is secured to block 40 only by screw 56, the ring and pins can be rotated about the screw about a central axis 64. This allows the angle of the pins to be adjusted to any desired value. A resilient washer in the form of wave washer 66 is provided between the head of screw 56 and ring 52 to maintain some pressure when the screw is loosened. This reduces unintentional slippage of the block on the pins while the fixator is being adjusted, while still allowing the block to be shifted up and down on, and rotated relative to the pins with the application of a modicum of force.

Figure 8:
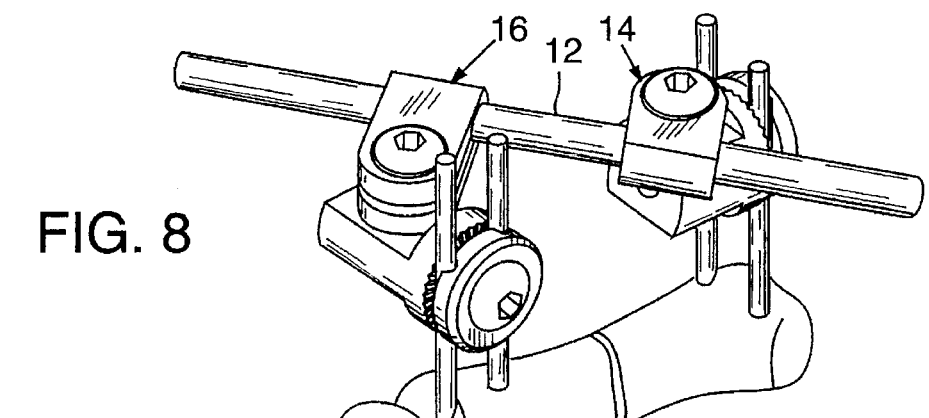
FIGS. 8 and 9 are perspective views of the fixator of FIG. 1 attached to a bone in two different configurations.
Figure 9:
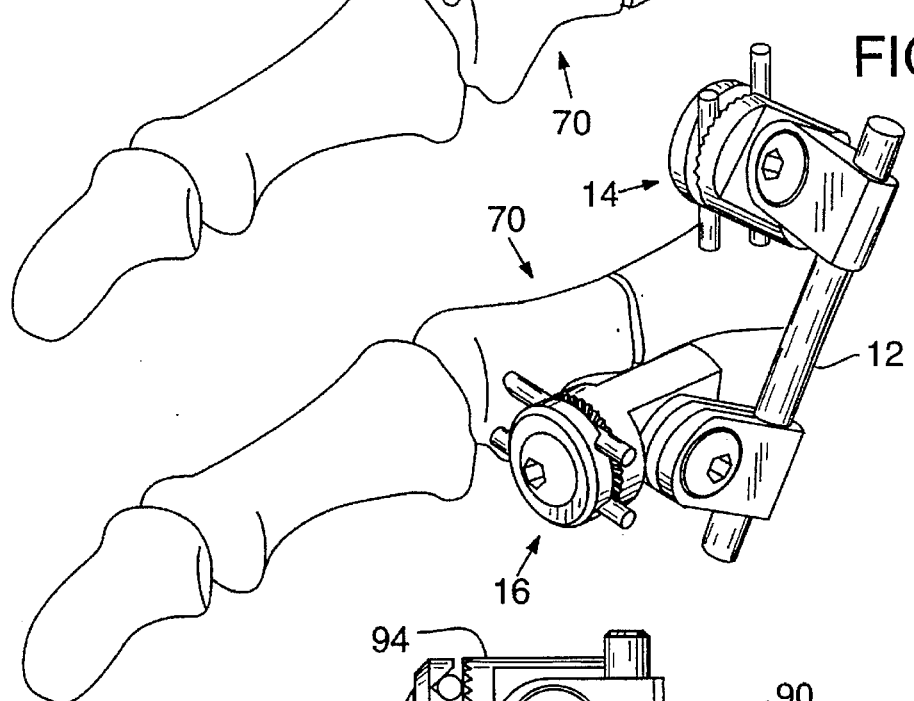

An example of how a fixator constructed according to the present invention may be applied is shown in FIG. 8. Fixator 10 is mounted on one of the proximal phalanges 70. Articulation assembly 14 is mounted on the proximal side of a fracture 72 and assembly 16 is mounted on the distal side. Note that assembly 14 has been flipped to the opposite side of rod 12 relative to the arrangement shown in FIGS. 1 and 2. As shown in FIG. 8, the flexibility of fixator 10 allows the pairs of pins to be installed with their axes in planes perpendicular to one another. The most desirable pin placement is often dictated by the nature of the injury and the desire to place the pins through uninjured skin. For instance, where the hand has been burned, there may only be a few locations of undamaged skin, thus severely restricting the placement of the pins. A second example of installation of the present fixator is shown in FIG. 9. In FIG. 9, the pairs of pins are placed perpendicularly to each other on the bone, further illustrating the flexibility of the fixator.

One of the principle goals of a fixator for use on the bones of the hand is compactness. Thus, the length of the support rod used in the present invention is chosen to accommodate the spacing between the articulation assemblies. In the preferred embodiment, a number of lengths of rod are provided and the surgeon simply selects the shortest rod which will connect the assemblies.

When installing the fixator of the present invention, the surgeon first chooses the pin locations and installs the pins as desired. After the pins are installed, the fixator is adjusted to fit over the pins. Because of the multiple degrees of freedom and geometry of the fixator, it is possible to accommodate virtually any pin placement geometry.

Figure 10:
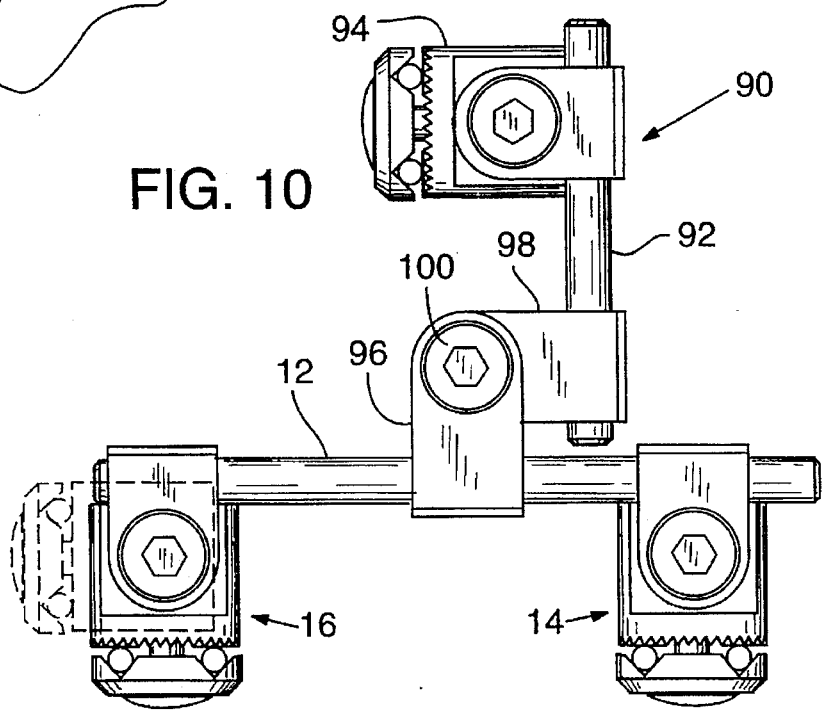
FIG. 10 is a top view of the fixator of FIG. 1 with an outrigger assembly attached.

For some applications, one or more outrigger assemblies, such as shown generally at 90 in FIG. 10, is desirable. Outrigger 90 includes a support rod 92 and at least one articulation assembly 94. Support rod 92 and articulation assembly 94 are interchangeable with support rod 12 and articulation assemblies 14 and 16 in the preferred embodiment. Support rod 92 is mounted to support rod 12 by two pivotally coupled rod clamps 96, 98. A screw 100 couples the clamps and, when tightened, locks the clamps to the rods and to each other. The clamps can slide along and rotate about the rods until the screw is tightened. As with the other screws, a wave washer 102 (not shown) is provided to maintain some pressure as the screw is loosened.

By using one or more outrigger assemblies it is possible to increase the rigidity of the fixation. Use of outriggers also increases the flexibility when treating multiple fracture injuries. For example, if several adjacent phalanges are fractured, it is possible to build a fixator assembly that can reduce the fractures and achieve greater stability by using multiple attachment points on several bones.

It will now be clear that an improvement in this art has been provided which accomplishes the objectives heretofore set forth. While the invention has been disclosed in its preferred form, it is to be understood that the specific embodiment thereof, as disclosed and illustrated herein, is not to be considered in a limited sense, as there are other forms or modifications which should also be construed to come within the scope of the appended claims.

I claim:

1. A compact external fixator comprising:
   an elongate cylindrical support rod;
   first and second rod clamps mounted to the support rod, the rod clamps having a loosened condition in which they can rotate about and translate along the elongate axis of the rod, and a tightened condition in which they are substantially fixed relative to the rod;
   first and second pin carrier blocks, one mounted to each rod clamp with each carrier block being pivotally moveable relative to the rod clamp to which it is mounted about a first pivot axis offset from and substantially perpendicular to the elongate axis of the rod, the pivotal movement between the carrier blocks and the rod clamps being selectively lockable to fix or release the relative pivotal position therebetween, each carrier block further including a generally planar circular pin mounting shelf with a central axis normal to the plane of the shelf, where the plane of the shelf is substantially parallel to and offset from the first pivot axis;

first and second pin clamp rings, each pin clamp ring being generally planar and disk-like and including an inner face in which are formed a pair of spaced apart, parallel pin guide tracks, each pin clamp ring further being disposed centered coaxially over the central axis of one of the pin shelves with the inner face oriented toward, generally parallel to and spaced apart from the pin shelf to capture therebetween a pair of pins, of the pin guide tracks being adapted to receive the pins with the pin clamp ring and pins being rotatable relative to the pin shelf about the central axis when the pin clamp ring is loosened and fixed relative to the pin shelf when the pin clamp ring is tightened.

2. The fixator of claim 1 wherein the pin shelf is serrated to improve the grip on the pins.

3. The fixator of claim 1 wherein the pivot axes between the rod clamps and the pin carrier blocks are offset from the longitudinal axis of the rod between one-eighth and one-half inches.

4. The fixator of claim 1 wherein the pivot axis between the rod clamps and the pin carrier blocks is offset from the planes of the pin shelves between one-eighth and one-half inches.

5. The fixator of claim 1 wherein the rod clamps are U-shaped with a closed end and two legs separated by a slot, each clamp including a cylindrical passage near the closed end adapted to fit over the rod so that when the legs are urged toward one another the rod clamp grips the rod creating the tightened condition and when the legs are not urged toward one another the rod clamp can rotate about and translate along the rod.

6. The fixator of claim 5 wherein the pin carrier blocks are attached to the rod clamps by screws disposed coaxially with the pivot axis between the pin carrier blocks and the rod clamps and tightening the screws creates the tightened condition.

7. The fixator of claim 6 wherein each screw has a head and a deformable washer is provided under the head of the screw to allow the screw to be loosened partially while still maintaining some pressure.

8. The fixator of claim 1 wherein the pin shelves have substantially the same radius as the pin clamp.

9. The fixator of claim 8 wherein the pin shelves and clamp rings are between one-quarter of an inch and one inch in diameter.

10. The fixator of claim 1 wherein, for each pin carrier block, a central plane is defined by the plane in which the central axis moves as the pin carrier block is rotated about the first pivot axis and the elongate axis of the rod is offset from and parallel to the central plane.

11. The fixator of claim 10 wherein the offset between the central planes and the elongate axis of the rod is between one-eighth of an inch and one-half an inch.

12. The fixator of claim 1 wherein the pin clamp rings are secured over the pins by screws which are coaxial with the central axes of the pin shelf.

13. The fixator of claim 12 wherein the screw includes a head and a deformable washer is provided under the head of the screw to maintain some pressure between the pin clamp ring and the pin shelf even when the screw is loosened slightly.

14. The fixator of claim 1 further including an outrigger assembly with a second support rod and a third rod clamp attached to the second support rod, a third pin carrier block attached to the third rod clamp and a third pin clamp ring attached to the third pin carrier ring, the second support rod being rotatably and slideably coupled to the support rod.

15. The fixator of claim 14 wherein the support rods are coupled by a pair of rod clamps, one rod clamp being disposed over each support rod and the two rod clamps being pivotally connected to each other.

* * * * *